United States Patent
Prisco et al.

(10) Patent No.: US 8,957,367 B2
(45) Date of Patent: *Feb. 17, 2015

(54) SHAPE SENSOR CONTAINED IN A LINK OF A KINEMATIC CHAIN WITH AT LEAST ONE PRE-SET PERTURBATION AND METHOD TO SENSE RELATIVE PARTIAL-POSE INFORMATION USING THE SHAPE SENSOR

(75) Inventors: Giuseppe Maria Prisco, Mountain View, CA (US); Theodore W. Rogers, Alameda, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1199 days.

This patent is subject to a terminal disclaimer.

(21) Appl. No.: 12/617,995

(22) Filed: Nov. 13, 2009

(65) Prior Publication Data

US 2011/0118749 A1    May 19, 2011

(51) Int. Cl.
*G01J 1/04* (2006.01)
*A61B 19/00* (2006.01)

(52) U.S. Cl.
CPC ......... *A61B 19/22* (2013.01); *A61B 2019/2223* (2013.01); *A61B 2019/467* (2013.01); *A61B 2019/5259* (2013.01); *A61B 2019/5261* (2013.01)
USPC ..................................... 250/227.14; 250/221

(58) Field of Classification Search
USPC ...... 250/221, 227.14–227.16, 227.22, 237 R, 250/559.33; 356/614, 615; 385/12, 13; 700/245; 600/104–117, 145, 424
See application file for complete search history.

(56) References Cited

U.S. PATENT DOCUMENTS

| | | | |
|---|---|---|---|
| 5,368,015 A * | 11/1994 | Wilk | 600/104 |
| 7,930,065 B2 * | 4/2011 | Larkin et al. | 700/245 |
| 2001/0021843 A1 | 9/2001 | Bosselmann et al. | |
| 2003/0209096 A1 | 11/2003 | Pandey et al. | |
| 2006/0013523 A1 | 1/2006 | Childers et al. | |
| 2006/0142657 A1 | 6/2006 | Quaid et al. | |
| 2007/0156019 A1 | 7/2007 | Larkin et al. | |
| 2008/0212082 A1 | 9/2008 | Froggatt et al. | |

FOREIGN PATENT DOCUMENTS

| | | |
|---|---|---|
| JP | 7049221 A | 2/1995 |
| WO | WO0113060 A1 | 2/2001 |
| WO | WO2008094949 A2 | 8/2008 |
| WO | WO2008131303 A2 | 10/2008 |

OTHER PUBLICATIONS

Alpuim, P., et al., "Ultra-Sensitive Shape Sensor Test Structures Based on Piezo-Resistive Doped Nanocrystalline Silicon", *NanoSpain Conference*, Apr. 14-18, 2008, 2 pages, Braga-Portugal.

(Continued)

*Primary Examiner* — Que T Le

(57) ABSTRACT

A shape-sensing segment traverses through at least a portion of a kinematic chain of a tele-operated slave surgical instrument in a tele-operated minimally-invasive surgical system. The shape-sensing segment includes a pre-set perturbation. Shape information from the pre-set perturbation allows determination of relative partial-pose information for at least one link in the kinematic chain.

27 Claims, 10 Drawing Sheets

(56) References Cited

OTHER PUBLICATIONS

Dakin, John P., "Distributed Optical Fibre Sensors", *Proceedings SPIE OE/Fibers '92 Conference Track Critical Reviews, Boston*, 1992, pp. 162-199, vol. 44(10), Pub No. 651, University of Southampton, Southampton, UK.

Duindam, Vincent, et al., "Method and System to Sense Relative Partial-Pose Information Using a Shape Sensor", U.S. Appl. No. 12/618,082, filed Nov. 13, 2009.

Udd, Eric, "Fiber Optic Smart Structures", *Proceedings of the IEEE*, Jan. 1996, pp. 60-67, vol. 84, No. 1, IEEE.

Vertut, Jean and Philippe Coiffet, *Teleoperation and Robotics: Evolution and Development*, 1986, 332 pages, English translation: Prentice-Hall, Inc., Inglewood Cliffs, NJ, USA.

PCT/US10/55569 International Search Report and Written Opinion of the International Searching Authority, mailed Jan. 26, 2011, 10 pages.

PCT/US10/56460 International Search Report and Written Opinion of the International Searching Authority, mailed Jun. 20, 2011, 8 pages.

U.S. Appl. No. 12/618,082 Office Action mailed Oct. 27, 2011, 13 pages.

International Search Report and Written Opinion for Application No. PCT/US2010/55569, mailed Jan. 26, 2011, 9 pages.

\* cited by examiner

SHAPE SENSOR CONTAINED IN A LINK OF A KINEMATIC CHAIN WITH AT LEAST ONE PRE-SET PERTURBATION AND METHOD TO SENSE RELATIVE PARTIAL-POSE INFORMATION USING THE SHAPE SENSOR

BACKGROUND

1. Field of Invention

Aspects of this invention are related to sensing information to characterize a kinematic chain in a minimally-invasive surgical instrument used in a tele-operated minimally-invasive surgical systems, and more particularly to shape sensors used to obtain relative pose information of links in such a kinematic chain.

2. Related Art

Optical fiber shape sensors are known. See e.g., U.S. Pat. No. 5,798,521 (filed 27 Feb. 1997), U.S. Pat. No. 6,389,187 B1 (filed 17 Jun. 1998), U.S. Patent Application Pub. No. US 2006/0013523 A1 (filed 13 Jul. 2005), and Roger G. Duncan et al., *Characterization of a Fiber-Optic Shape and Position Sensor*, Smart Structures and Materials 2006: Smart Sensor Monitoring Systems and Applications (D. Inaudi et al. eds.), 6167 *Proceedings of SPIE* 616704 (16 Mar. 2006), all of which are incorporated by reference. Optical fiber shape sensors have been used to sense joint angles in a minimally invasive surgical instrument. See, e.g., U.S. Patent Application Pub. No. US 2007/0156019 A1 (filed 20 Jul. 2006) and NASA Tech Briefs, *NASA-Inspired Shape-Sensing Fibers Enable Minimally Invasive Surgery* (1 Feb. 2008), http://www.techbriefs.com/content/view/2585/, both of which are incorporated herein by reference.

Typically, optical fiber shape sensors operate via optical time domain reflectometry (OTDR) or via optical frequency domain reflectometry (OFDR). Most approaches use a backscatter method that measures changes in backscattered light caused by a change in the shape of the optical fiber. Scattering mechanisms that have been used include Rayleigh scattering, Raman scattering, Brillouin scattering, and Fluorescence scattering. Fiber Bragg Gratings and the Kerr effect have also been used in shape-sensing sensors.

Other techniques have also been used for shape sensing. For example, electromagnetic fields have been used in combination with sensors mounted on an endoscope to determine a position of an endoscope. See U.S. Patent Application Publication No. 2007/0249901 A1 (filed Mar. 28, 2006; disclosing "Instrument Having Radio Frequency Identification Systems and Methods for Use."), which is incorporated herein by reference in its entirety. Also, the changes in resistance of a piezoresistive flexible shape sensor have been used to measure shape changes.

SUMMARY

A shape sensor within a link in a kinematic chain of a minimally-invasive slave-surgical instrument provides shape information that can be analyzed to determine joint angle(s) of the kinematic chain and relative positions of links in the kinematic chain. In one aspect, a minimally-invasive tele-operated surgical system includes a minimally-invasive slave surgical instrument. The slave surgical instrument, in turn, includes a kinematic chain having a proximal link and a distal link. A shape-sensing segment extends through at least one of the proximal link and the distal link. The shape-sensing segment includes at least one pre-set perturbation, sometimes referred to as a shape sensor, located within one of the proximal link and the distal link.

In one aspect, the at least one pre-set perturbation is a geometrical perturbation fixed in the shape-sensing segment. The pre-set perturbation has a geometrical center identifiable by shape sensor measurements. Also, the pre-set perturbation is in a geometrical plane identifiable by shape sensor measurements. Further, in one aspect, the preset perturbation includes another preset-perturbation. The another pre-set perturbation is in a second geometrical plane identifiable by the shape sensor measurements.

The pre-set geometrical perturbation can be formed, for example, by a clamp affixed to the shape-sensing segment. The pre-set geometrical perturbation has a geometrical center in a fixed geometrical relationship with one of the proximal link and the distal link. Also the pre-set geometrical perturbation has a geometrical plane identifiable by shape sensor measurements, and is in a fixed geometrical relationship with one of the proximal link and the distal link. Also, in one aspect, the preset geometrical perturbation includes another preset-perturbation. The another pre-set perturbation has a second geometrical plane, identifiable by the shape sensor measurements, in a fixed geometrical relationship with the other of the proximal link and the distal link.

In another aspect, a pre-set geometrical feature is fixed in position with respect to the distal link. The at least one pre-set perturbation is formed in the shape-sensing segment by the pre-set geometrical feature as the pre-set geometrical feature is moved along the shape-sensing segment. Thus, the at least one pre-set perturbation moves relative to the proximal link as the distal link moves. The pre-set geometrical feature is formed, for example, in a wall of a lumen through which the shape-sensing segment passes.

In one embodiment, an interrogator is coupled to the shape-sensing segment. The interrogator outputs shape information associated with the shape-sensing segment including the at least one pre-set perturbation. An electronic data processor is coupled to the interrogator to receive the shape information. The electronic data processor analyzes the shape information and outputs relative partial-pose information of at least one of the distal link and the proximal link.

In one aspect, the output relative partial-pose information is a linear displacement. In another aspect, the output relative partial-pose information is an angle. In yet another aspect, the output relative partial-pose information is three-dimensional position and orientation.

In still another aspect, the at least one pre-set perturbation is positioned within the proximal link. The shape-sensing segment also includes another pre-set perturbation, different from the at least one pre-set perturbation. The another pre-set perturbation is positioned within the distal link.

In one aspect of the kinematic chain with two pre-set perturbations, a roll link is mounted in the kinematic chain between the proximal link and the distal link. In this aspect, the output relative partial-pose information is a roll angle associated with the roll link.

In another aspect of the kinematic chain with two pre-set perturbations, the at least one known-shape perturbation is included in a first plane. The another known-shape perturbation is included in a second plane. The relative partial-pose information is an angle of the second plane relative to the first plane.

The above described apparatus is used in a process that receives shape data from at least one pre-set perturbation in a shape-sensing segment. The shape-sensing segment passes through at least one of a proximal link and a distal link of a kinematic chain. A processor generates relative partial-pose information of at least one of the distal link and the proximal link from the received shape data.

In another aspect, the pre-set perturbation is a mechanically-constrained known transition in a shape-sensing segment as the shape-sensing segment passes between a proximal link and a distal link of a kinematic chain. In one aspect, the proximal link includes a body defining a first lumen extending through the proximal link. The first lumen has a first axis. The shape-sensing segment passes through the first lumen. The distal link includes a body defining a second lumen extending through the distal link. The second lumen has a second axis. The shape-sensing segment passes into the second lumen to form the mechanically-constrained known transition.

In one aspect, the proximal link includes a body defining a first lumen extending through the proximal link. The first lumen has a first axis. The shape-sensing segment passes through the first lumen. The distal link includes a body defining a second lumen extending through the distal link. The second lumen has a second axis. The shape-sensing segment passes into the second lumen to form an angle. The angle is the mechanically-constrained known transition.

An interrogator coupled to the shape-sensing segment. The interrogator outputs shape information for the mechanically-constrained known-transition in the shape-sensing segment. An electronic data processor is coupled to the interrogator to receive the shape information. The electronic data processor outputs relative partial-pose information for the proximal link and the distal link.

The above described apparatus is used in a process that receives information from a mechanically-constrained known-transition in a shape-sensing segment. The shape-sensing segment passes through a proximal link and a distal link of a kinematic chain and the mechanically-constrained known-transition is between the proximal and distal links. The process generates relative partial-pose information for the proximal link and the distal link.

Thus, rather than use a shape-sensing segment to sense bends in a kinematic chain, a pre-set perturbation, e.g., a pre-set bend, in the shape-sensing segment is used to determine relative partial-pose information for at least one link in the kinematic chain, e.g., a displacement, the location of the link, an angle of link with respect to another link in the kinematic chain, or the three-dimensional position and orientation.

Figure 1A:
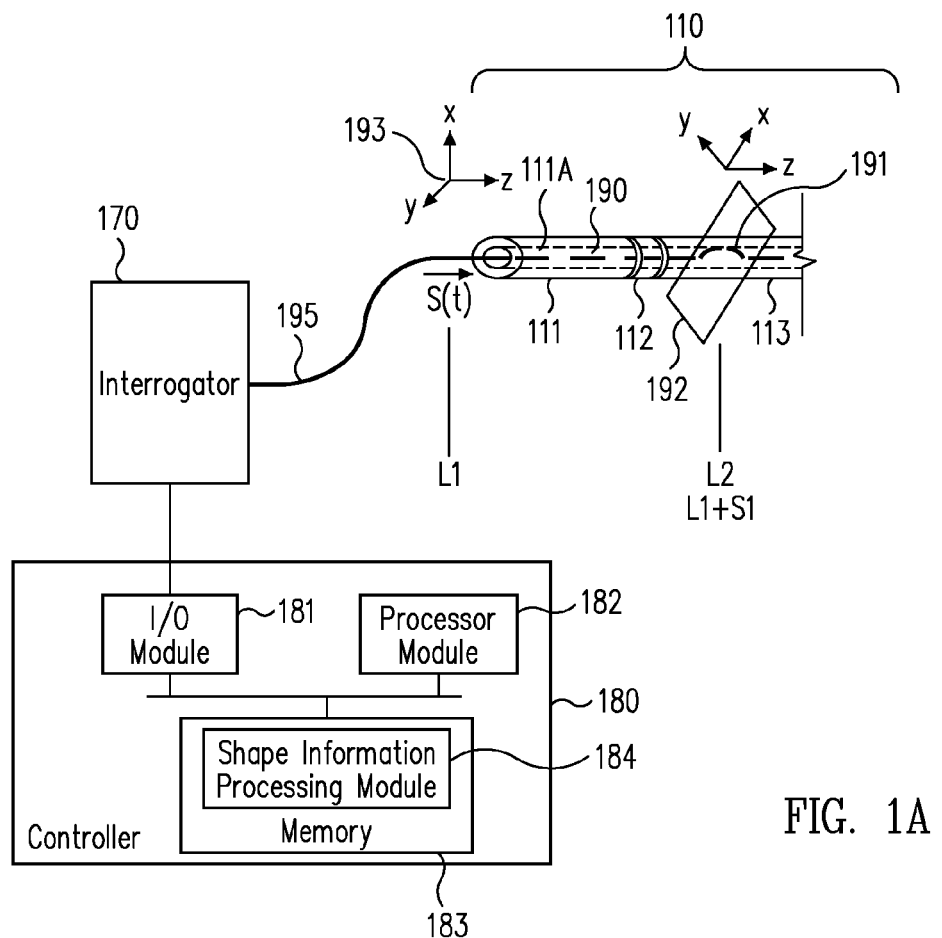
FIG. 1A is a diagrammatic view of a portion of a minimally-invasive surgical system which includes a minimally invasive slave surgical instrument with a kinematic chain including a shape sensor.

In the drawings, the first digit of a figure number indicates the figure in which the element with that figure number first appeared.

DETAILED DESCRIPTION

Aspects of this invention include a shape-sensing segment 190 (FIG. 1A) traversing through at least a portion of a kinematic chain 110 of a tele-operated slave surgical instrument 130 (FIG. 1B) in a tele-operated minimally-invasive surgical system. Shape-sensing segment 190 includes a pre-set perturbation 191. Shape information from pre-set perturbation 191 allows determination of relative partial-pose information for at least one link in kinematic chain 110. Thus, rather than use shape-sensing segment 190 to sense bends in a kinematic chain 110, a pre-set perturbation 191, e.g., a pre-set bend, in shape-sensing segment 190 is used to determine relative partial-pose information for at least one link in kinematic chain 110, e.g., the location of link 113, an angle of link 113 with respect to another link in kinematic chain 110, or both. In one aspect, the three-dimensional pose (position and orientation) of a link is obtained.

The ability to obtain the partial-pose information permits, as explained more completely below, determining the roll associated with a roll joint in the kinematic chain. In addition, since a location of a fixed point on pre-set perturbation 191, sometimes referred to as a geometrical center, can be measured and pre-set perturbation 191 is fixed within link 113, a location of link 113 can be determined.

Thus, the pre-set bend, i.e., pre-set perturbation 191, functions as a shape sensor for a particular link or links in kinematic chain 110. Shape information from the pre-set bend is analyzed by a processor to generate and output the relative partial-pose information for that particular link or links.

The ability to determine the relative partial-pose information of a distal link with respect to a proximal link in kinematic chain 110 during use of tele-operated slave surgical instrument 130 provides new capabilities in providing feedback to a surgeon using tele-operated slave surgical instrument 130. The relative partial-pose information is obtained without having to make any guesses as to the shape and/or orientation of kinematic chain 110.

In the examples described more completely below, a shape-sensing segment of an optic fiber and Optical Frequency Domain Reflectometry are considered. In particular, the shape-sensing segment utilizes Fiber Bragg Gratings. The use of Fiber Bragg Gratings is illustrative only and is not intended to be limiting to this specific mechanism for creating backscatter. In view of this disclosure, other optic fiber shape-sensing technologies could be used including but not limited to Rayleigh scattering, Raman scattering, and Brillouin scattering.

Further, the use of an optic fiber shape-sensing segment is also illustrative and is not intended to be limiting. In view of this disclosure, other shape-sensing technologies could be used including but not limited to an electromagnetic field based shape-sensing segment and a piezoresistive based shape-sensing segment. For a particular type of shape-sensing segment, the pre-set perturbation is configured as described below, and an interrogator for that shape-sensing segment is used. The data from the interrogator is processed using techniques equivalent to those described more completely below to obtain the relevant partial pose. Accordingly, as stated previously, the following examples are illustrative of using a pre-set perturbation in a shape-sensing segment to generate partial-pose information and are not intended to be limiting to the specific shape-sensing segments described.

FIG. 1A is an illustration of part of a kinematic chain 110 that includes a proximal link 111 and a distal link 113 coupled by a single degree of freedom (DOF) revolute joint 112, which is illustrative of various movable mechanical constraints of one or more degrees of freedom, e.g., prismatic, cylindrical, screw, planar, spherical, etc., that may couple two links 111, 113 to allow various relative movements. In one aspect, joint 112 allows distal link 113 to move in a single plane with reference to link 111.

Shape-sensing segment 190 of multi-core optic fiber 195, sometimes referred to as optic fiber 195, is routed through kinematic chain 110 and in particular through at least proximal link 111, joint 112, and into distal link 113. As shown in FIG. 1A, shape-sensing segment 190 passes through a lumen 111A that extends through each of links 111, 113 and joint 112 in this example. For example, lumen 111A can be positioned along the centerlines of links 111, 113, e.g., embedded in a polytetrafluoroethylene (PTFE) tube that is placed in a central bore in links 111, 113 and joint 112. While in this example, lumen 111A is along a common axis in each of links 111, 113 and joint 112, this configuration is illustrative only and is not intended to be limiting to this specific configuration.

In this example, pre-set perturbation 191 is located and fixed within link 113. Pre-set perturbation 191 has a geometrical center that is identifiable by shape sensor measurements. Also, pre-set perturbation 191 lies in a geometrical plane 192 that also is identifiable by shape sensor measurements. Since pre-set perturbation 191 is fixed within link 113, geometrical plane 192 is said to have a fixed geometrical relationship with link 113 in that the angle of the plane gives the angle of the link, as discussed more completely below.

In one example, optic fiber 195 is a three core optic fiber, as described more completely below. In other embodiments, various numbers of cores may be used.

Interrogator 170 interrogates optic fiber 195 and provides shape information from shape-sensing segment 190 to an input/output module 181 in controller 180. In particular, a shape signature for pre-set perturbation 191 is provided in the shape information.

The shape information is analyzed as a function of a discretized curvilinear coordinate S(t). A processor in a processor module 182 of controller 180 executes computer instructions in a shape information processing module 184 stored in memory 183. The processor determines the curvilinear coordinate center of pre-set perturbation 191. The processor then performs an integration from the location of reference frame 193 at position L1 to the geometrical center of pre-set perturbation at position L2. In one aspect, the location of the geometrical center of pre-set perturbation 191 is determined by finding the center of the shape signature representing pre-set perturbation 191.

The integration (See expression (15) below) generates the x-y-z position of pre-set perturbation 191 at location L2, which in turn can be used to determine the relative position and angle of the geometrical center of pre-set perturbation 191 relative to reference frame 193, in this example. The relative position and angle of pre-set perturbation 191 is the relative partial-pose information of link 113. Thus, in this example, relative partial-pose information of distal link 113 with respect to the proximal link 111 of kinematic chain 110 has been determined using the shape information from pre-set perturbation 191.

In one example, the shape information from pre-set perturbation 191 is differential strain information. The differential strain information can be processed by the processor to give orthogonal local bend information $$\begin{bmatrix} \theta_{x,n} \\ \theta_{y,n} \end{bmatrix}$$

between locations L1 and L2 of shape-sensing segment 190.

In this example, optic fiber 195 has N Fiber Bragg Gratings continuously written at a spacing of Δd at least between locations L1 and L2. Here, N is an integer number. Orthogonal local bend information $$\begin{bmatrix} \theta_{x,n} \\ \theta_{y,n} \end{bmatrix}$$

is defined for curvilinear coordinate S(t), where S=Δd*n, and n ranges from one to N. A summary of how to determine orthogonal local bend information $$\begin{bmatrix} \theta_{x,n} \\ \theta_{y,n} \end{bmatrix},$$

in one aspect, is provided below.

In this aspect, interrogator 170 interrogates optic fiber 195 and provides shape information from optic fiber 195 to controller 180, as described above. Interrogator 170 implements Optical Frequency Domain Reflectometry technology with a standard Optic Backscatter Reflectometer for each core in optic fiber 195.

As discussed more completely below, instructions executing on a processor in controller 180 integrate information derived from orthogonal local bend information $$\begin{bmatrix} \theta_{x,n} \\ \theta_{y,n} \end{bmatrix}$$

between locations L1 and L2 to obtain coordinates ($x_n$, $y_n$, $z_n$), relative to a reference frame at location L1 at each point n along optic fiber 195, where n ranges from one to N.

The integration generates the relative position and orientation of the fiber core reference frame at curvilinear coordinate L1+S1, which is the geometrical center of pre-set perturbation 191, with respect to the reference coordinate system at position L1. A more detailed description of one process used to obtain coordinates ($x_n$, $y_n$, $z_n$) at curvilinear coordinate L1+S1 is described in copending and commonly assigned U.S. Patent Application Publication No. US 2009/0324161 A1, of U.S. patent application Ser. No. 12/164,829, entitled "FIBER OPTIC SHAPE SENSOR," of Giuseppe M. Prisco, and filed on Jun. 30, 2008, now U.S. Pat. No. 7,720,322 B2, which is incorporated herein by reference in its entirety.

Figure 1C:
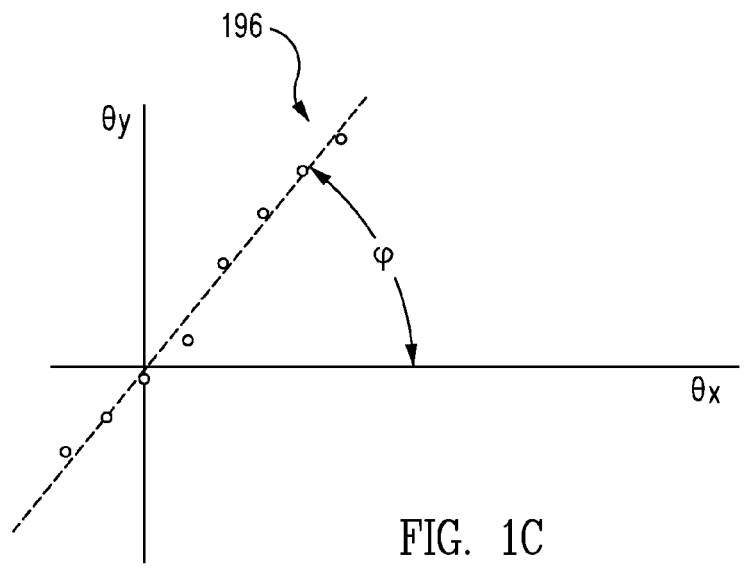
FIG. 1C is an illustration of one embodiment of how a processor in a controller of the minimally-invasive surgical system determines a relative angle of a link in the kinematic chain.
Figure 1B:
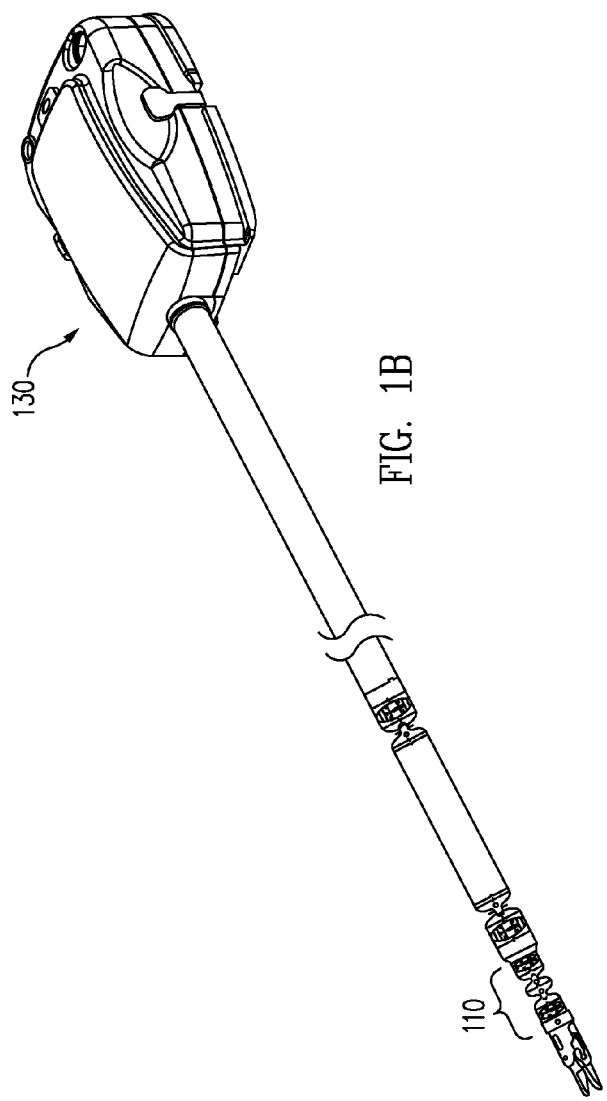
FIG. 1B is a diagrammatic view of the minimally invasive slave surgical instrument with a kinematic chain including a shape sensor.

In one embodiment, as orthogonal local bend information $$\begin{bmatrix} \theta_{x,n} \\ \theta_{y,n} \end{bmatrix}$$

is obtained for n from 1 to N by controller 180, orthogonal local bend information $$\begin{bmatrix} \theta_{x,n} \\ \theta_{y,n} \end{bmatrix}$$

at each point is plotted with $\theta_{y,n}$ along the vertical axis and $\theta_{x,n}$ along the horizontal axis. See FIG. 1C.

When the data generated by analyzing the shape information from specific pre-set perturbation 191, in this example, is plotted, the data defines a straight line 196. Angle φ of straight line 196 is the angle of geometrical plane 192 containing pre-set perturbation 191 relative to optic fiber 195. In the example of FIG. 1A, optic fiber 195 runs along the rotational axis of links 111 to 113. Pre-set perturbation 191 is fixed in link 113 and so in this example, angle φ is the rotation of link 113 with respect to link 111.

Thus, using a pre-set perturbation 191 allows the sensing of relative position and angle of link 113. Pre-set perturbation 191 can take many different forms. In one aspect, pre-set perturbation 191 can be a pre-set geometric perturbation such as a S-curve, a loop, a cusp, a semi-circle, etc formed at a specific location in shape-sensing segment 190. Pre-set perturbation 191 can also be a fixed transition between a proximal link and a distal link, or a fixed transition at a fixed angle between a proximal link and a distal link.

Pre-set perturbation 191 can be a clamp or other device mounted on shape-sensing segment 190 that provides a known shape signature with interrogated. Alternatively, the angle, transition, and pre-set geometric shape can be formed using one or more clamps or other devices mounted on shape-sensing segment 190. In this aspect, pre-set perturbation 191 is a fixed shape in shape-sensing segment 190 and the shape of pre-set perturbation 191 does not change as the pose of kinematic chain 110 changes.

Figure 1D:
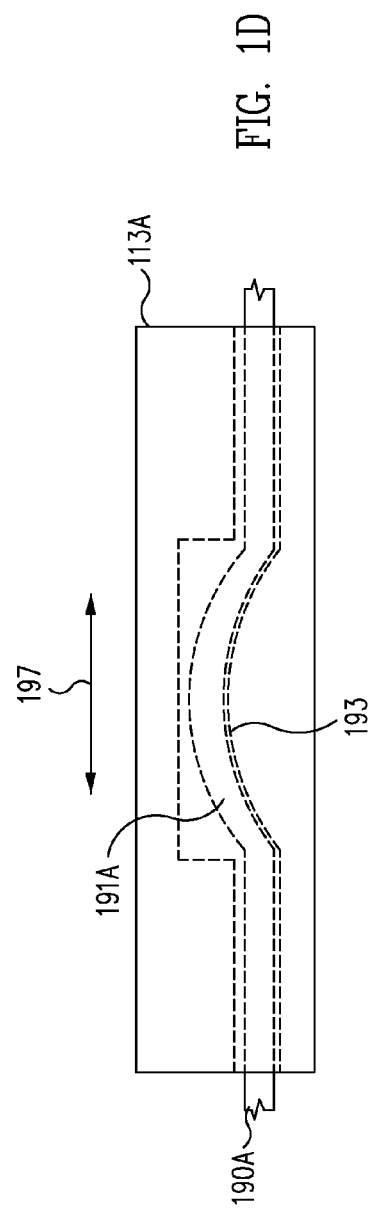
FIG. 1D is an illustration of one embodiment a link in a kinematic chain that includes a pre-set geometrical feature.

In another aspect, the fixed shape of pre-set perturbation 191A (FIG. 1D) is formed in shape-sensing segment 190A by a pre-set geometrical feature 193 of a particular link 113A of the kinematic chain. In this example, link 113A can move along shape-sensing segment 190A in the z-direction as indicated by arrow 197. When link 113A, and consequently pre-set geometrical feature 193, is moved along shape-sensing segment 190A, the geometrical center of pre-set perturbation 191A also moves along shape-sensing segment 190A. The technique described herein for determining the relative partial-pose information of a link is directly applicable to link 113A and can be used to generate the relative pose of link 113A with respect to another link.

Thus, the pre-set perturbation can be formed by making a permanent pre-set shape in the shape-sensing segment itself, or alternatively can be formed by a permanent pre-set geometric feature in a link over which the shape-sensing segment passes. In the following examples, the pre-set perturbation can be formed by using either of these methods. The particular method utilized typically depends on the functionality of the links and joints for which the pre-set perturbation is used to determine the relative partial-pose information of a distal link with respect to a proximal link in the kinematic chain of a minimally-invasive slave surgical instrument.

Figure 2A:
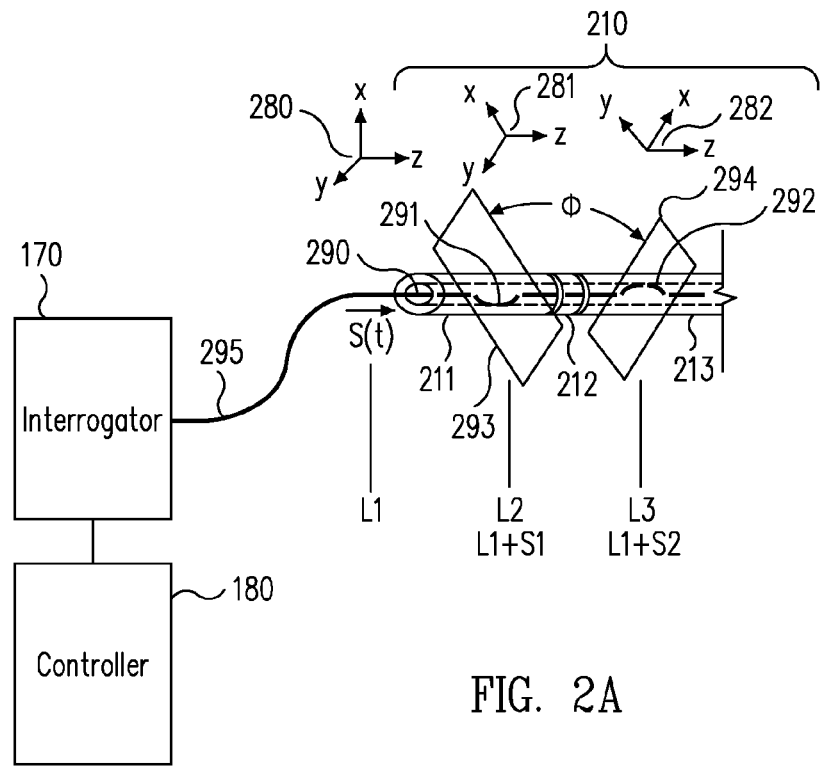
FIG. 2A is a diagrammatic view of a portion of a minimally-invasive surgical system which includes a minimally invasive slave surgical instrument with a kinematic chain including a shape sensor in a distal link and a shape sensor in a proximal link.

In FIG. 2A, the pre-set perturbation has two parts: a first pre-set perturbation 291 and a second pre-set perturbation 292. As illustrated in FIG. 2A, part of a kinematic chain 210 includes a proximal link 211 and a distal link 213 coupled by a single degree of freedom (DOF) revolute joint 212. Joint 212 is illustrative of various movable mechanical constraints of one or more degrees of freedom, e.g., prismatic, cylindrical, screw, planar, spherical, etc., that may couple two links 211, 213 to allow various relative movements. In one aspect, joint 212 allows distal link 213 to move in a single plane with reference to link 211.

Shape-sensing segment 290 of multi-core optic fiber 295, sometimes referred to as optic fiber 295, is routed through kinematic chain 210 and in particular through at least proximal link 211, joint 212, and into distal link 213. As shown in FIG. 2A, shape-sensing segment 290 passes through a lumen that extends through each of links 211, 213 and joint 212 in this example.

For example, the lumen can be positioned along the centerlines of links 211, 213, e.g., embedded in a PTFE tube that is placed in a central bore in links 211, 213 and joint 212. While in this example, the lumen is along a common axis in each of links 211, 213 and joint 212, this configuration is illustrative only and is not intended to be limiting to this specific configuration.

In this example, first pre-set perturbation 291 is located within link 211. Second pre-set perturbation 292 is located within link 213. Thus, first pre-set perturbation 291 is removed from second pre-set perturbation 292. Each of pre-set perturbations 291, 292 has a geometrical center that is identifiable by shape sensor measurements. Also, each of pre-set perturbations 291, 292 lies in a geometrical plane 293, 294, respectively that also is identifiable by shape sensor measurements. Since pre-set perturbation 291 is fixed within link 211, geometrical plane 291 is said to have a fixed geometrical relationship with link 211 in that the angle of the plane gives the angle of the link, as discussed more completely below. Also, since pre-set perturbation 292 is fixed within link 213, geometrical plane 294 is said to have a fixed geometrical relationship with link 213 in that the angle of the plane gives the angle of the link, as discussed more completely below.

Also, in this example, optic fiber 295 is a three core optic fiber, as described more completely below. In other embodiments, various numbers of cores may be used.

In one example, the shape information from pre-set perturbations 291 and 292 is differential strain information. The differential strain information can be processed by a processor to give orthogonal local bend information $$\begin{bmatrix} \theta_{x,n} \\ \theta_{y,n} \end{bmatrix}$$

between locations L1 and L3. Optic fiber 295 is similar to optic fiber 195 with respect to the Fiber Bragg Gratings and curvilinear coordinate S(t), where S=Δd*n, and n ranges from one to N.

In this aspect, interrogator 170 interrogates optic fiber 295 and provides shape information to controller 180, as described above. Interrogator 170 implements Optical Frequency Domain Reflectometry technology with a standard Optic Backscatter Reflectometer for each core in optic fiber 295.

As discussed more completely below, instructions executing on a processor in controller 180 can determine the location of the geometrical centers of pre-set perturbations 291 and 292. The processor also integrates information derived from orthogonal local bend information $$\begin{bmatrix} \theta_{x,n} \\ \theta_{y,n} \end{bmatrix}$$

between locations L1 and L3 of shape-sensing segment 290 to obtain coordinates ($x_n$, $y_n$, $z_n$), relative to a reference frame 280 at location L1 at each point n, where n ranges from one to N.

The integration generates the relative coordinates at curvilinear coordinate L1+S1, which is the geometrical center of pre-set perturbation 291, with respect to reference coordinate system 280 at position L1.

Figure 2B:
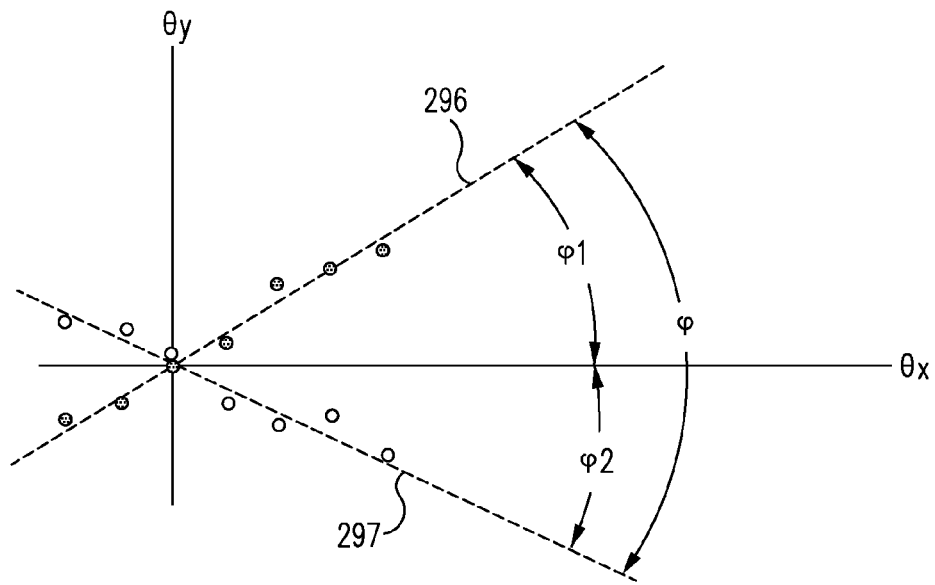
FIG. 2B is an illustration of one embodiment of how a processor in a controller of the minimally-invasive surgical system determines a relative angle of the distal link with respect to the proximal link in the kinematic chain of FIG. 2A.

In one embodiment, as orthogonal local bend information $$\begin{bmatrix} \theta_{x,n} \\ \theta_{y,n} \end{bmatrix}$$

is obtained for n from 1 to N by controller 180, orthogonal local bend information $$\begin{bmatrix} \theta_{x,n} \\ \theta_{y,n} \end{bmatrix}$$

at each point is plotted with $\theta_{y,n}$ along the vertical axis and $\theta_{x,n}$ along the horizontal axis. See FIG. 2B. When the data generated from the shape information from pre-set perturbations 291 and 292, in this example, is analyzed by the processor, the data defines a straight line 296, 297 corresponding to each of the pre-set perturbations 291, 292. Angle φ1 of straight line 296 for pre-set perturbation 291 is the angle of link 211 with respect to reference frame 280. Angle φ2 of straight line 297 for pre-set perturbation 292 is the angle of link 211 with respect to reference frame 280.

By relating angles φ1 and φ2 in links 211, and 213, angle φ, between plane 293 containing pre-set perturbation 291 in link 211 and plane 294 containing pre-set perturbation 292 in link 213, can be determined by the processor. When joint 212 is a roll joint, angle φ is the roll angle and so gives the relative partial-pose information of distal link 213 with respect to proximal link 211.

Figure 2C:
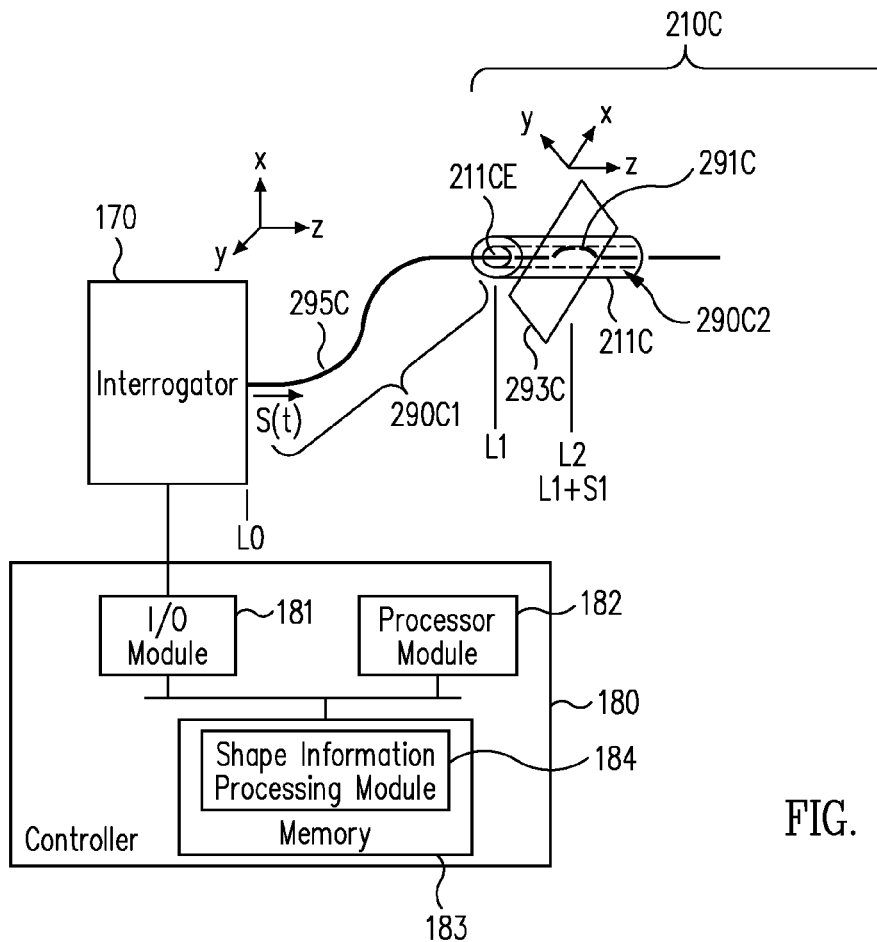
FIG. 2C is a diagrammatic view of a portion of a minimally-invasive surgical system which includes a minimally invasive slave surgical instrument with a kinematic chain including a shape sensor in a link and a shape-sensing segment between the link and a base.

FIG. 2C is an illustration of part of a kinematic chain 210C that includes a link 211C. A first shape-sensing segment 290C1 of multi-core optic fiber 295C, sometimes referred to as optic fiber 295, extends from a base of optic fiber 295C at interrogator 170 to an entry point 211CE of link 211C. A second shape-sensing segment 290C2 of optic fiber 295C extends through link 211C and includes pre-set perturbation 291C.

Pre-set perturbation 291C has a geometrical center that is identifiable by shape sensor measurements. Also, pre-set perturbation 291C lies in a geometrical plane 293C that also is identifiable by shape sensor measurements. Since pre-set perturbation 291C is fixed within link 211C, geometrical plane 292C is said to have a fixed geometrical relationship with link 211C in that the angle of the plane gives the angle of the link, as discussed more completely below.

As shown in FIG. 2C, second shape-sensing segment 290C2 passes through a lumen that extends through link 211C and is positioned along the centerline of link 211C, e.g., embedded in a polytetrafluoroethylene (PTFE) tube that is placed in a central bore in link 211C.

Interrogator 170 interrogates optic fiber 295C and provides shape information from shape-sensing segments 290C1, 290C2 to an input/output module 181 in controller 180. The shape information is analyzed as a function of a discretized curvilinear coordinate S(t). A processor in a processor module 182 of controller 180 executes computer instructions in a shape information processing module 184 stored in memory 183. The processor analyzes the data from first shape-sensing segment 290C1 to determine the three-dimensional orientation of fiber 295C at entry point 211CE. (See expression (13) below.) The processor also performs an integration from the base of first shape-sensing segment 29001 to entry point 211CE. The integration (See expression (15) below) generates the x-y-z position at entry point 211CE of link 211C, which is the start of link 211C. Thus, a x-y-z position and a three-dimensional orientation have been determined at entry point 211CE.

However, the x-y-z position and the three-dimensional orientation determined for entry point 211CE may not represent the actual position and orientation of link 211C because fiber 295C may slide and roll inside link 211C. Hence, the shape information from pre-set perturbation 291C in shape-sensing segment 290C2 is analyzed to obtain the actual position and orientation of link 211C.

The strain trace from pre-set perturbation 291C is analyzed to determine the location of the geometrical center of pre-set perturbation 291C from entry point 211CE. Since the location of pre-set perturbation 291C is fixed with respect to link 211C, the location of the geometrical center of pre-set perturbation 291C is used to offset the x-y-z position determined for entry point 211CE to obtain the x-y-z position of link 211C.

The shape information from pre-set perturbation 291C is differential strain information. The differential strain information is processed by the processor to give orthogonal local bend information $$\begin{bmatrix} \theta_{x,n} \\ \theta_{y,n} \end{bmatrix}.$$

Figure 2D:
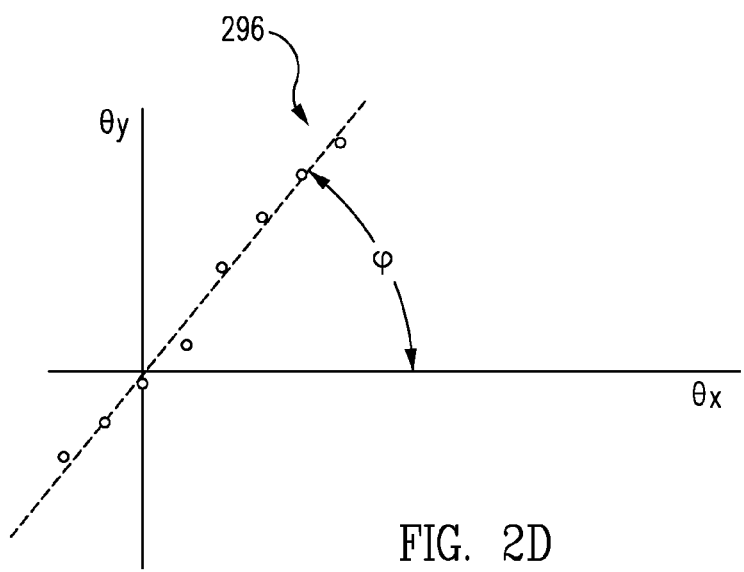
FIG. 2D is an illustration of one embodiment of how a processor in a controller of the minimally-invasive surgical system determines an angle of the distal link.

The orthogonal local bend information $$\begin{bmatrix} \theta_{x,n} \\ \theta_{y,n} \end{bmatrix}$$

is plotted with $\theta_{y,n}$ along the vertical axis and $\theta_{x,n}$ along the horizontal axis. See FIG. 2D.

When the data generated by analyzing the shape information from specific pre-set perturbation 291C, in this example, is plotted, the data defines a straight line 296. Angle ϕ of straight line 296 is the angle of plane 293C containing pre-set perturbation 291C relative to optic fiber 295C.

In the example of FIG. 2C, optic fiber 295C runs along the rotational axis of link 211C. Pre-set perturbation 291C is fixed within link 211C and so in this example, angle ϕ is the rotation of link 211C, i.e., the roll. Angle ϕ of geometrical plane 293C containing pre-set perturbation 291C is used to offset the roll determined for entry point 211CE to obtain the roll of link 211C. Thus, the x-y-z position and the yaw, pitch and roll orientations are known for link 211C. The configuration in FIG. 2C using a pre-set perturbation 291C in a second shape-sensing segment in combination with a first shape-sensing segment allows determination of the three-dimensional position and orientation of link 211C. Note that in FIG. 2C, first shape-sensing segment 290C1 is not shown as passing through any other links in kinematic chain 210C, segment 290C1 can pass through one or more links.

Figure 2E:
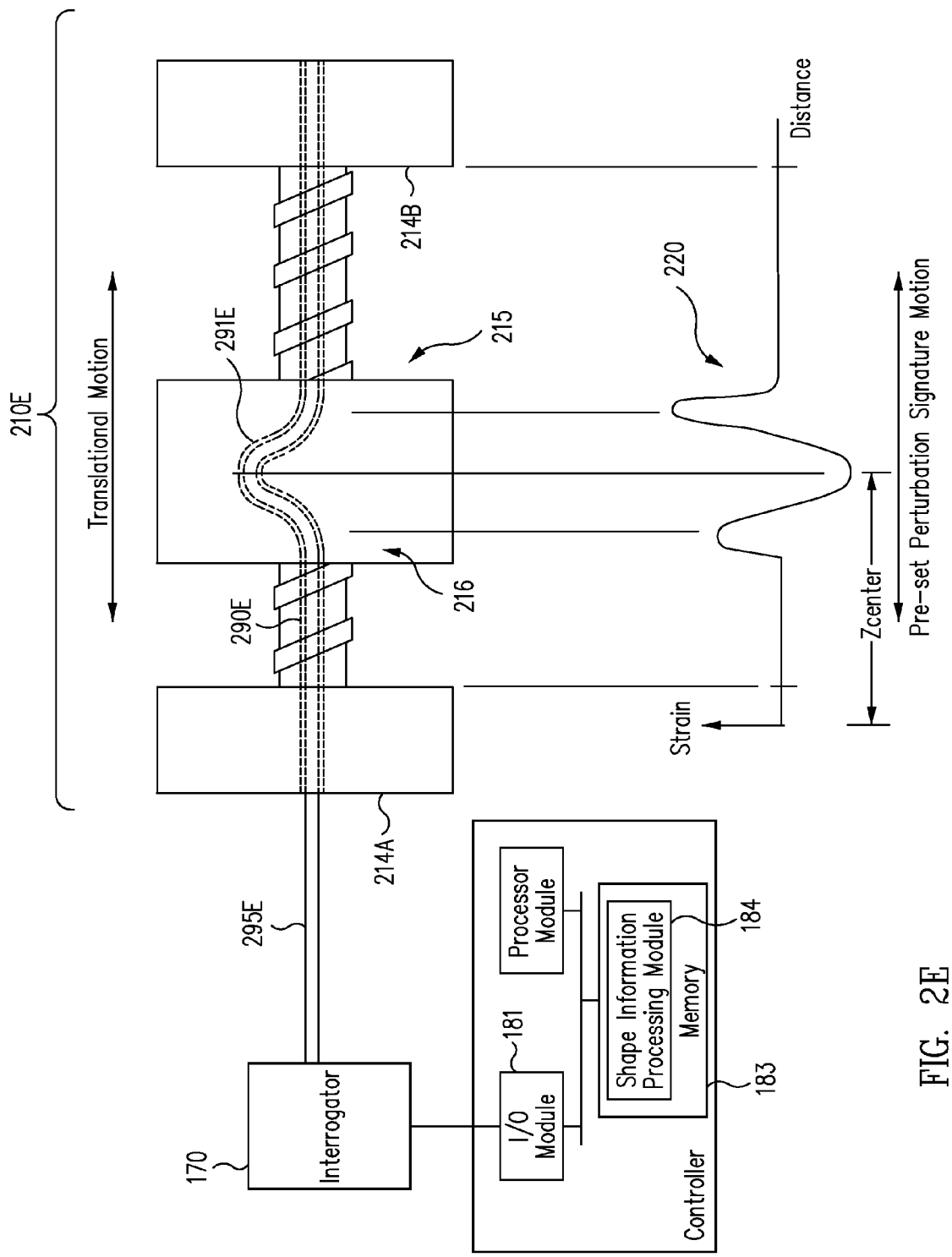
FIG. 2E is a diagrammatic view of a portion of a minimally-invasive surgical system which includes a minimally invasive slave surgical instrument with a kinematic chain including a shape sensor in a link and a prismatic joint.

FIG. 2E is an illustration of yet another kinematic chain 210E that includes a first link that in turn includes a first base element 214A and a second base element 214B, a prismatic joint 215 and a second link 216. First base element 214A and a second base element 214B function as bases for prismatic joint 215.

A shape-sensing segment 290E of a multi-core optic fiber 295C extends through base element 214A and prismatic joint 215, link 216 and into base element 214B. The base of shape-sensing segment 290E is in base element 214A. Shape-sensing segment 290E includes pre-set perturbation 291E, which has a geometrical center that can be determined by shape measurements and is located within link 216.

As link 216 is moved along prismatic joint 215 between base elements 214A and 214B, the geometrical center of pre-set perturbation 291E undergoes translational motion. Strain trace 220 for shape-sensing segment 290E is shown in FIG. 2E.

The distance from the base of shape-sensing segment 290E to the geometrical center of pre-set perturbation 291E is shown as distance Zcenter. As the geometrical center of pre-set perturbation 291E undergoes translational motion, trace 200 moves relative to the base and so distance Zcenter changes. Thus, trace 220 can be used to determine the location of link 216 as link 216 undergoes translational motion along prismatic joint 215.

Hence, the links in FIG. 2A, which each had a pre-set perturbation fixed therein, were used to determine the rotation angle between the links. The link in FIG. 2C with a pre-set perturbation fixed therein and a shape-sensing segment extending from the base of the optic fiber to the entry point of the link was used to determine the three-dimensional position and orientation of the link. Finally, in FIG. 2E, a preset-perturbation fixed within a link was used to determine the translational motion of the joint.

Figure 3A:
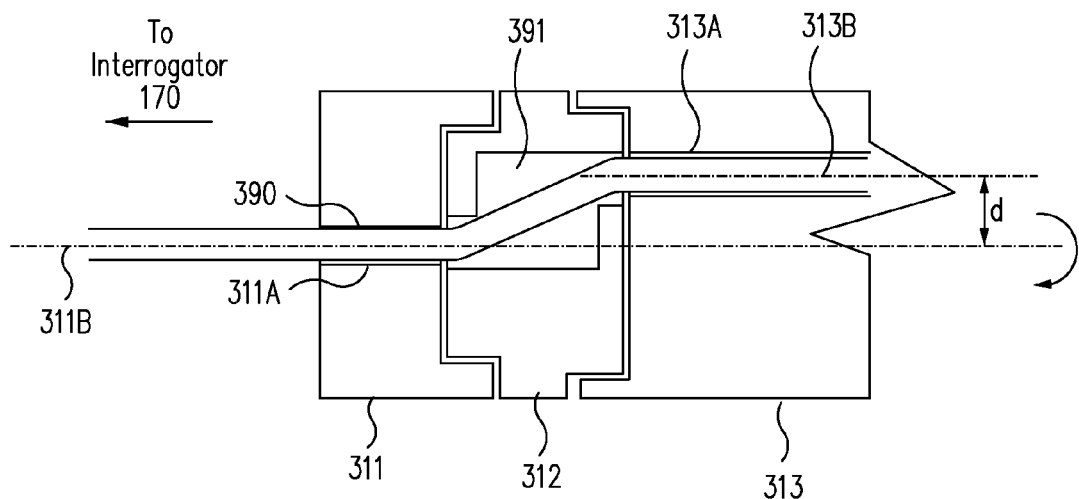
FIG. 3A is a diagrammatic view of a portion of a minimally-invasive surgical system which includes a minimally invasive slave surgical instrument with a kinematic chain including a mechanically-constrained fixed transition of a shape-sensing segment of an optic fiber between a proximal link and a distal proximal link.

In another example, the pre-set perturbation is a mechanically-constrained known-transition. In FIG. 3A, the transition as shape-sensing segment 390 passes from a distal link 311 into a proximal link 313 in a kinematic chain is referred to as a mechanically-constrained known-transition 391 and sometimes as mechanically-constrained transition 391. In this example, links 311 and 313 and a joint 312 are part of a kinematic chain similar to chain 110 in slave surgical instrument 130. Also, in one aspect, joint 312 allows distal link 313 to move in a single plane with reference to link 311.

Shape-sensing segment 390, sometimes referred to as segment 390, of a multi-core optic fiber is routed through the kinematic chain. In particular, segment 390 is routed through at least proximal link 311, joint 312, into distal link 313 so that mechanically-constrained transition 391 is formed in shape-sensing segment 390 between proximal link 311 and distal link 313.

As shown in FIG. 3A, shape-sensing segment 390 passes through a first lumen 311A in a body of link 311. Lumen 311A extends along a first axis 311B. Upon leaving lumen 311A, shape-sensing segment 390 transitions to and passes through a second lumen 313A in a body of link 313. Lumen 313A extends along a second axis 311B. (As used herein, first and second are not used in a numeric sense, but rather as adjectives to distinguish between the different axes.)

Lumen 311A and lumen 313A are tight fitting about shape-sensing segment 390 so that mechanically-constrained transition 391 is formed in shape-sensing segment 390 as shape-sensing segment 390 transitions from proximal link 311 into distal link 313. While lumen 313A is tight fitting, lumen 313A is also configured so that the optic fiber can freely twist within lumen 313A. Torsion in the optic fiber due to friction between the cladding of the optic fiber and the wall of lumen 313A is not measured in one aspect, but such torsion results in hysteresis or other non-linearities between the actual relative partial-pose information of the distal link with respect to the proximal link and the measured relative partial-pose information of the distal link with respect to the proximal link.

In this example, axis 311B is an axis of rotation of proximal link 311. Axis 313B is offset from and parallel to axis 311B by a distance d. This configuration is illustrative only and is not intended be limiting. Axis 311B can be other than the axis of rotation, for example. Also, it is not essential that two axes are parallel so long as mechanically-constrained known-transition 391 can be identified in the shape information obtained from shape-sensing segment by interrogator 170. Irrespective of the location of the axis of proximal link 311, axis 313B is offset from the axis of rotation.

Figure 3B:
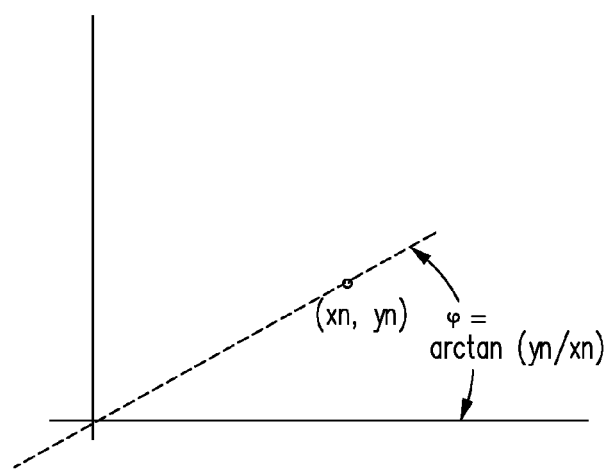
FIG. 3B is an illustration of one embodiment of how a processor in a controller of the minimally-invasive surgical system determines a relative angle of the distal link with respect to the proximal link in the kinematic chain of FIG. 3A.

In this example, the common frame of reference is defined with respect to proximal link 311. As described above, the shape information for shape-sensing segment 390 is provided to a processor in controller 180 by interrogator 170. As described above and as described more completely below, the processor integrates the shape information to obtain the x-y coordinates (xn, yn) of shape-sensing segment 390 in distal link 313. The processor then takes arctan(yn/xn) to generate angle ϕ (FIG. 3B). Here, the arctangent function is represented by arctan. When joint 312 is a roll joint, angle ϕ is the joint roll angle.

In yet another example, the pre-set perturbation is an angle $\zeta$ of a mechanically-constrained transition 491 in a shape-sensing segment 490 as shape-sensing segment 490 passes from a distal link 411 into a proximal link 413 in a kinematic chain. In this example, angle $\zeta$ is the mechanically-constrained known-transition. In this example, links 411, 413 and a joint 412 are part of a kinematic chain similar to chain 110. Also, in this example, joint 412 allows distal link 413 to move in a single plane with reference to link 411.

Shape-sensing segment 490, sometimes referred to as segment 490, of a multi-core optic fiber is routed through the kinematic chain. In particular, segment 490 is routed through at least proximal link 411 and joint 412 into distal link 413 so that angle $\zeta$ of mechanically-constrained transition 491 is formed in shape-sensing segment 490 between proximal link 411 and distal link 413. In this example, a clamp 492, e.g., a tight-fitting tube, is mounted on shape-sensing segment 490 so that clamp 492 maintains shape-sensing segment 490 at angle $\zeta$ in mechanically-constrained transition 491.

Figure 4:
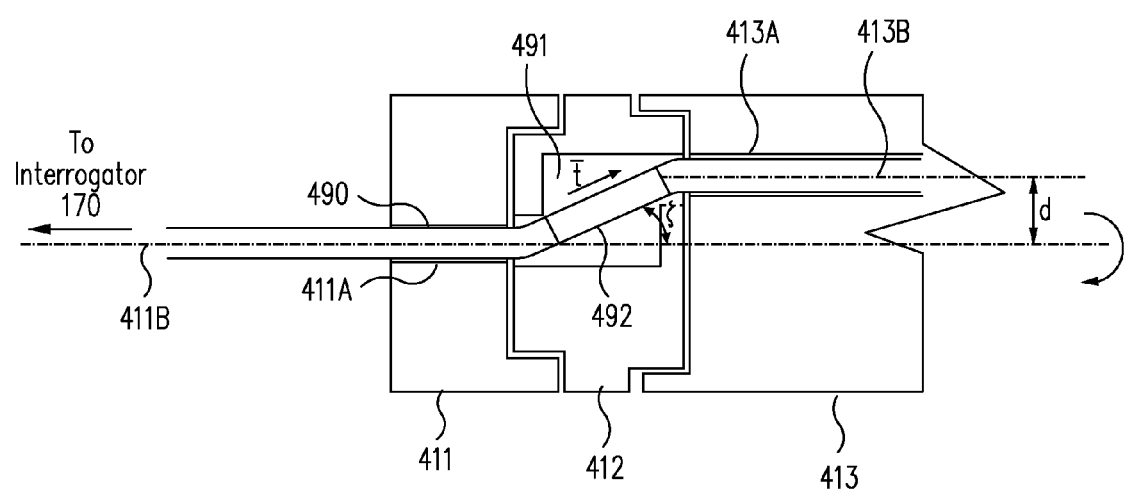
FIG. 4 is a diagrammatic view of a portion of a minimally-invasive surgical system which includes a minimally invasive slave surgical instrument with a kinematic chain including a mechanically-constrained fixed transition at a pre-set angle of a shape-sensing segment between a proximal link and a distal proximal link.

As shown in FIG. 4A, shape-sensing segment 490 passes through a first lumen 411A in a body of link 411. Lumen 411A extends along a first axis 411B. Upon leaving lumen 411A, shape-sensing segment 490 transitions to and passes through a second lumen 413A in a body of link 413. Lumen 413A extends along a second axis 413B. (As used herein, first and second are not used in a numeric sense, but rather as adjectives to distinguish between the different axes.) Second axis 413B is offset from the axis of rotation, which in the example of FIG. 4B is axis 411B. In this example, angle $\zeta$ is the angle formed by the intersection of the centerline of segment 490 in the transition with first axis 411B.

Lumen 411A and lumen 413A are tight fitting about shape-sensing segment 490 so that angle of mechanically-constrained transition 491 is formed in shape-sensing segment 490 as shape-sensing segment 490 transitions from proximal link 411 into distal link 413. While lumen 413A is tight fitting, lumen 413A is also configured so that the optic fiber can freely twist within lumen 413A. Torsion in the optic fiber due to friction between the cladding of the optic fiber and the wall of lumen 413A is not measured in one implementation, but such torsion results in hysteresis or other non-linearities between the actual relative partial-pose information of the distal link with respect to the proximal link and the measured relative partial-pose information of the distal link with respect to the proximal link.

In this example, axis 411B is an axis of rotation of proximal link 411. Axis 413B is offset from and parallel to axis 411B by a distance d. This configuration is illustrative only and is not intended be limiting. Axis 411B can be other than the axis of rotation, for example. Also, it is not essential that two axes are parallel so long as angle $\zeta$ of mechanically-constrained transition 491 can be identified in the shape information obtained from shape-sensing segment 490 by interrogator 170.

The processor in controller 180 determines tangent vector $\vec{t}$ at a point inside clamp 492. One expression for tangent vector E is given below in expression (13). Tangent vector $\vec{t}$ provides the angle of link 413. When joint 412 is a roll joint, the angle is the joint roll angle. A steeper angle $\zeta$ relative to axis 411B gives a more precise measurement than a shallower angle $\zeta$ relative to axis 411B.

Thus, a shape sensor, e.g., a pre-set perturbation in a shape-sensing segment of an optic fiber traversing a plurality of links in a kinematic chain of a minimally-invasive slave-surgical instrument, provides shape information that can be analyzed to determine joint angle(s) of the kinematic chain. As described above for FIG. 3A, a twist-insensitive shape sensor and mechanical constraints in a rolling joint offsets the position of the shape sensor away from the axis of rotation on at least one of the connecting links. Thus, a change of the roll angle of the joint results in a change in lateral position of the shape sensor. As described above for FIG. 4A, a twist-insensitive shape sensor and mechanical constraints in a rolling joint offsets the position of the shape sensor away from the axis of rotation on at least one of the connecting links. In this aspect, a change of the roll angle of the joint results in a change in the pointing direction of the shape sensor not parallel to the axis of rotation.

Figure 5:
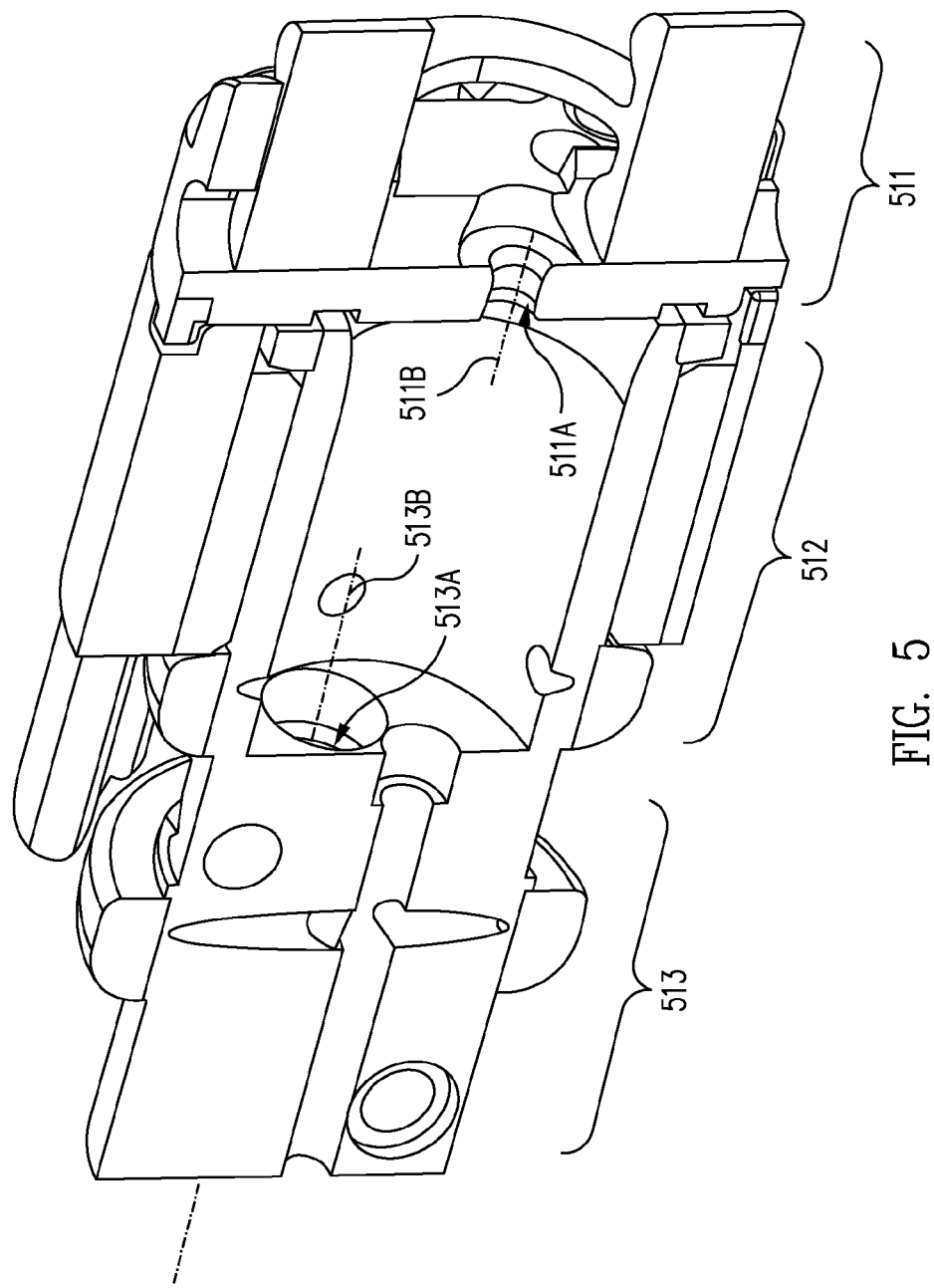
FIG. 5 is an example of embodiment of a proximal link, a roll joint and a distal link that can be utilized according to the embodiments of FIGS. 3A and 4.

FIG. 5 is a cross-sectional view of a portion of a kinematic chain that includes a proximal link 511, a roll joint 512, and a distal link 513 that can be used in the implementation of the aspects described with respect to either FIG. 3A or 4A. Proximal link 511 has a lumen 511A. See also, copending and commonly assigned U.S. Patent Application Publication No. US 2010/0160929 A1, of U.S. patent application Ser. No. 12/342,396, entitled "A ROLL JOINT AND METHOD FOR A SURGICAL APPARATUS," of Theodore W. Rogers et al., and filed on Dec. 23, 2008, which is incorporated herein by reference in its entirety.

While it is not illustrated in FIG. 5, the shape-sensing segment would pass through a first lumen 511A in a body of link 511. Lumen 511A extends along a first axis 511B. Upon leaving lumen 511A, the shape-sensing segment would transition into a second lumen 513A in a body of link 513. Lumen 513A extends along a second axis 513B. First axis 511B is different from second axis 513B, which means that axis 511B and second axis 513B are not different parts of a same axis. Axis 513B is offset from axis 511B.

Figure 6:
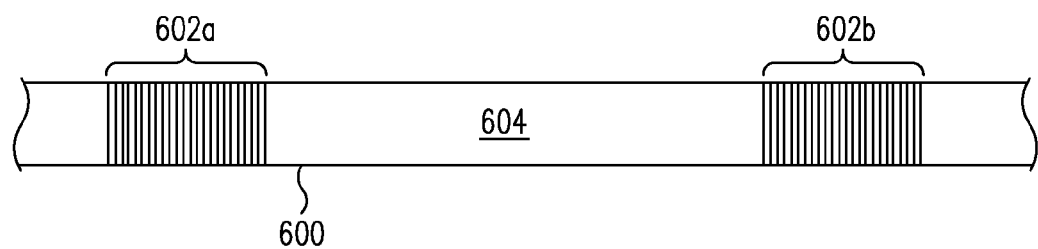
FIG. 6 is a diagrammatic view of an optic fiber core portion.

FIG. 6 is a diagrammatic view of an optical fiber core portion 600. The surrounding cladding and fiber are omitted for clarity. Two Fiber Bragg Gratings 602a, 602b are shown formed in fiber core portion 600, which are illustrative of many such Fiber Bragg Gratings typically formed along the full length of a core. The many vertical lines shown in each Fiber Bragg Grating 602a, 602b represent the changes in refractive index that characterize a Fiber Bragg Grating. As shown in FIG. 6, the Fiber Bragg Gratings 602a, 602b are separated by a tether segment 604, which is completely transmissive.

Figure 7:
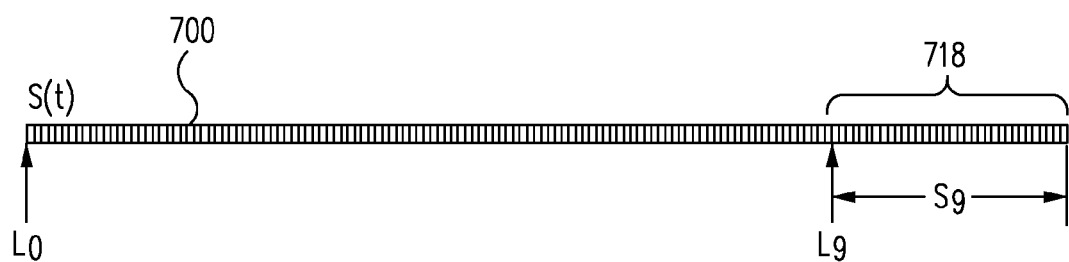
FIG. 7 is a diagrammatic view of an optic fiber core.

FIG. 7 is a diagrammatic view of one configuration of an optic fiber core 700. Other configurations are illustrated in copending and commonly assigned U.S. Patent Application Publication No. US 2009/0324161 A1, of U.S. patent application Ser. No. 12/164,829, entitled "FIBER OPTIC SHAPE SENSOR," of Giuseppe M. Prisco, and filed on Jun. 30, 2008, which was previously incorporated herein by reference in its entirety.

In. FIG. 7, the surrounding cladding and fiber are omitted for clarity. Each of the many vertical lines shown represents individual, adjacent Fiber Bragg Gratings. As described below, each core is one core of three or more cores in a single optic fiber.

As indicated above and shown in FIG. 7, a curvilinear coordinate system S(t) is defined for the fiber, and hence for core 700 and the other cores (not shown). In some cases, location $L_0$ of the origin of coordinate system S(t) is defined at the proximal end of the optic fiber, where the optic fiber connects to interrogator unit 170. In other cases, the origin location $L_0$ of coordinate system S(t) may be defined at a location along the optic fiber. For example, origin location $L_0$ may be defined at a location within a base mechanical link of a kinematic chain at which the fiber is fixed during manufacturing.

Once origin location $L_0$ is defined, one or more shape-sensing segments are defined between locations along the core. Each defined shape-sensing segment of a core contains part of one Fiber Bragg Grating, or one full Fiber Bragg Grating, or many adjacent Fiber Bragg Gratings. As shown in FIG. 7, core 700 has Fiber Bragg Gratings defined along its entire length, with shape-sensing segment 718 is defined at the distal end of the core, with no additional segments defined in the Fiber Bragg Grating-configured core. Shape-sensing segment starts at location $L_9$ and extends for a distance $S_9$. In the above examples, the pre-set perturbation or perturbations are formed in shape-sensing segment 718 in one aspect.

Figure 8:
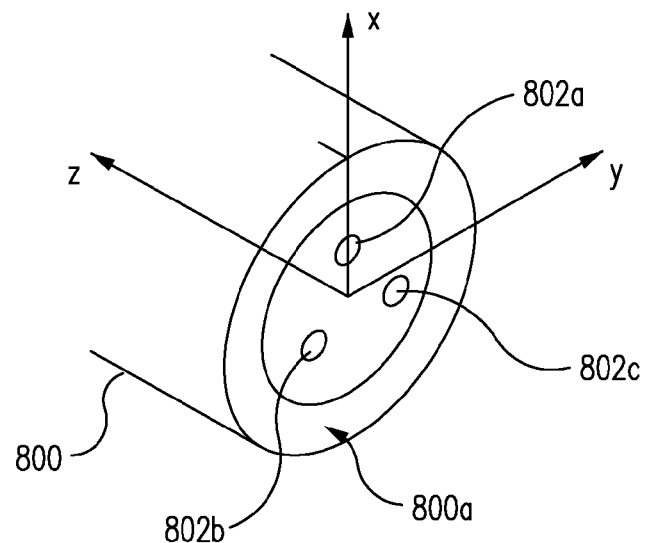
FIG. 8 is a diagrammatic view of the proximal end of an optic fiber with an illustrative reference frame.

FIG. 8 is a diagrammatic view of the proximal end of an optic fiber 800 with an illustrative reference frame defined. As shown in FIG. 8, fiber 800 has three Fiber Bragg Grating-configured cores 802a, 802b, 802c within a cladding layer 800a. Each core 802a, 802b, 802c is positioned at an apex of an equilateral triangle centered in optic fiber 800.

As shown in FIG. 8, a Cartesian reference frame is defined for the optic fiber 800. One axis of the Cartesian reference frame intersects one of the cores (the x-axis is shown intersecting core 802a as an illustration) and another axis is tangent to the centerline of optic fiber 800 (the z-axis is shown as an illustration). Defining the x-axis to extend through a core provides a rotational reference around the centerline of optic fiber 800. The definition of the x-axis is arbitrary and can be based on the geometry of the kinematic chain embedding the optic fiber. For instance, the x-axis could be aligned to one joint axis of the kinematic chain in which the optic fiber is embedded or associated.

The Cartesian reference frame (x, y, z) shown in FIG. 8 functions as a base frame when defined with an origin coincident with the origin of the curvilinear coordinate system S(t). When a Cartesian reference frame is defined with an origin at a segment start location, the Cartesian reference frame functions as a shape-sensing segment reference frame. A Cartesian reference frame may be similarly defined at a segment end location. Although three cores are shown in FIG. 8, other numbers of cores may be used (e.g., two opposite cores for planar bend measurement, four cores to measure fiber twist, etc.).

Figure 9:
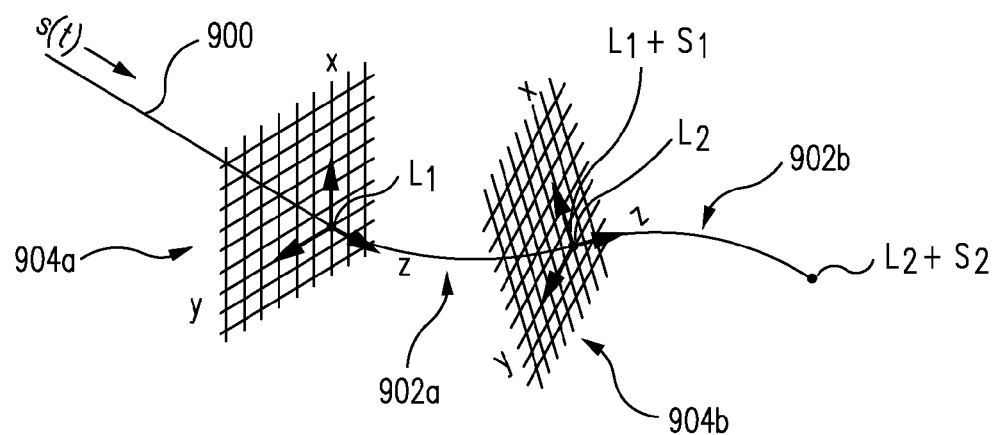
FIG. 9 is a diagrammatic view that illustrates reference frames at segment start locations in an optical fiber used for shape sensing.

FIG. 9 is a diagrammatic view that illustrates reference frames at segment starts in an optical fiber used for shape sensing. FIG. 9 depicts an optical fiber 900 that is, in one embodiment, configured with three cores as illustrated in FIG. 8 (four cores or other core configurations may be used). Two shape-sensing segments are defined in optic fiber 900. A first segment 902a is defined from curvilinear reference location $L_1$ (segment start) to curvilinear reference location $L_1+S_1$ (segment end). The second segment 902b is defined from curvilinear reference location $L_2$ (segment start) to curvilinear reference location $L_2+S_2$ (segment end). In accordance with an aspect of the invention, a first Cartesian reference frame 904a is defined at segment start $L_1$. The z-axis of reference frame 904a is tangent to the centerline of optic fiber 900 at segment start $L_1$. The x-axis of reference frame 904a runs through one of the cores as illustratively shown and described in FIG. 8. Similarly, a second Cartesian reference frame 904b is defined at segment start $L_2$, with the z-axis of reference frame 904b tangent to the centerline of optic fiber 900 at segment start $L_2$. The x-axis of reference frame 904b runs through the same core the x-axis of reference frame 904a.

The base reference frame illustrated in FIG. 8 and the two segment start reference frames illustrated in FIG. 9 are interrelated because all three have one normal axis (e.g., the x-axis) defined through the same core (e.g., core 902a).

The following is an illustration of computations carried out by an electronic data processing unit, sometime simply call a processor, in controller 180. Skilled individuals will understand that many hardware, firmware, and software options exist for constructing an electronic data processing unit, and that implementation of necessary computations will be routine in light of this description.

The expression for the local strain $\epsilon(s)$ is written as a function of distance along a given fiber core, $$\epsilon_n = \epsilon(\Delta d n) \quad (1)$$

where $\Delta d$ is the distance increment per index n. The $\Delta d$ value is set by the resolution of the OFDR-based interrogator. For instance the local strain $\epsilon(s)$ as a function of distance along each fiber core is obtained by making use of an "Optical Backscatter Reflectometer", a commercially available product from Luna Innovations Incorporated, Roanoke, Va., for each core. Such a device is able to output the phase derivative of the reflected light as a function of the distance along the fiber core, as shown in *Optical Backscatter Reflectometer User Guide* Chaps 5-6, 33-60 (Luna Technologies, Inc. 2004) (Document version 1.0 for OBR control software version 0.42 Beta), which is incorporated herein by reference. Such Phase Derivative information is proportional to the desired local strain $\epsilon(s)$ in expression (1).

For the pre-set perturbation, the differential strains between the cores are needed. For three cores, the required differential strains are:

$$\Delta \epsilon_{p,n} = \epsilon_{2,n} - \epsilon_{1,n} \quad (2a)$$

$$\Delta \epsilon_{q,n} = \epsilon_{3,n} - \epsilon_{1,n} \quad (2b)$$

where $\Delta \epsilon_p$ and $\Delta \epsilon_q$ designate the two differential strain arrays.

These differential strains can then be converted into local bends in an ortho-normal coordinate system by using a simple linear transformation, $$\begin{bmatrix} \theta_{x,n} \\ \theta_{y,n} \end{bmatrix} = \begin{bmatrix} m_{px} & m_{qx} \\ m_{py} & m_{qy} \end{bmatrix} \begin{bmatrix} \Delta \epsilon_{p,n} \\ \Delta \epsilon_{q,n} \end{bmatrix} \quad (3)$$

The m-matrix $\overline{\overline{m}}$ is a full description of the multi-core fiber, capturing the effects of the locations of the cores and the initial rotational orientation of the fiber in the coordinate system.

Next, these two rotation values are used to create a rotation matrix equal to the product of a first rotation of an angle $\theta_{x,n}$ around the x-axis and a second rotation of $\theta_{y,n}$ around the y-axis according to the equations:

$$\overline{\overline{R}}_{x,n} = \begin{bmatrix} 1 & 0 & 0 \\ 0 & \cos\theta & -\sin\theta \\ 0 & \sin\theta & \cos\theta \end{bmatrix} \quad (4)$$

$$\overline{\overline{R}}_{y,n} = \begin{bmatrix} \cos\theta & 0 & \sin\theta \\ 0 & 1 & 0 \\ -\sin\theta & 0 & \cos\theta \end{bmatrix}$$

$$\overline{\overline{R}}_n = \overline{\overline{R}}_{x,n} \overline{\overline{R}}_{y,n}$$

For small angle approximation, the above expression simplifies to:

$$\overline{R}_n = \begin{bmatrix} 1 & 0 & \theta_{y,n} \\ 0 & 1 & -\theta_{x,n} \\ -\theta_{y,n} & \theta_{x,n} & 1 \end{bmatrix} \quad (5)$$

where, because a first order small angle approximation is used, $\overline{R}_n$ is a valid rotation matrix only if $\theta_x \ll 1$ and $\theta_y \ll 1$.

If sufficiently small spatial increments are used, the above conditions are not difficult to satisfy. This rotation matrix is then moved into the coordinate system at the $n^{th}$ position on the fiber. In this way, the calculations are iterated to walk down the length of the fiber, reconstructing the tangent vector, as well as the vectors defining the rotational coordinate system, along the way. The iterative equation is, $$\overline{C_{n+1}} = \overline{C_n R_n} \quad (6)$$

Or, for the linearized case, $$\begin{bmatrix} C_{11} & C_{12} & C_{13} \\ C_{21} & C_{22} & C_{23} \\ C_{31} & C_{32} & C_{33} \end{bmatrix}_{n+1} = \begin{bmatrix} C_{11} & C_{12} & C_{13} \\ C_{21} & C_{22} & C_{23} \\ C_{31} & C_{32} & C_{33} \end{bmatrix}_n \begin{bmatrix} 1 & 0 & \theta_y \\ 0 & 1 & -\theta_x \\ -\theta_y & \theta_x & 1 \end{bmatrix}_n \quad (7)$$

And so, the coordinate system at any location along the array is given by, $$\overline{C}_p = \overline{C}_0 \overline{R}_0 \overline{R}_1 \overline{R}_2 \ldots \overline{R}_p = \overline{C}_0 \prod_{n=0}^{p} \overline{R}_n \quad (8)$$

The initial value of this coordinate system matrix, $$\overline{C}_0 = \begin{bmatrix} c_{11} & c_{12} & c_{13} \\ c_{21} & c_{22} & c_{23} \\ c_{31} & c_{32} & c_{33} \end{bmatrix}_0 \quad (9)$$

describes the initial orientation of the fiber in the exterior coordinate system. If the fiber is initially aligned along the z-axis, the matrix will be, $$\overline{C}_0 = \begin{bmatrix} \sin\beta & -\cos\beta & 0 \\ \cos\beta & \sin\beta & 0 \\ 0 & 0 & 1 \end{bmatrix}_0 \quad (10)$$

In the description above, the first two vectors still have one degree of freedom, which is the rotation of the fiber around its axis—the same rotational degree of freedom in the m-matrix above. This is because with three cores we cannot sense the fiber rotation around its axis. In many implementations, this situation is not generally a problem, because it will generally be taken care of automatically by the way the fiber is embedded in or associated with the kinematic chain and by calibration. Further, it means that complete generality can be retained even if the initial matrix is restricted to be, $$\overline{C}_0 = \begin{bmatrix} 1 & 0 & 0 \\ 0 & 1 & 0 \\ 0 & 0 & 1 \end{bmatrix}_0 \quad (11)$$

The tangent vector $\vec{t}$ is the last column of the $\overline{C}$ matrix, $$\vec{t} = \overline{C} \cdot \begin{bmatrix} 0 \\ 0 \\ 1 \end{bmatrix} \quad (12)$$

Accordingly, the tangent vector at any particular point is the product of all of the previous rotation vectors, $$\vec{t}_p = \overline{C}_0 \prod_{n=0}^{p} \overline{R}_n \cdot \begin{bmatrix} 0 \\ 0 \\ 1 \end{bmatrix} \quad (13)$$

The position at any point along the fiber is the sum of all of the previous tangent vectors, multiplied by the length of fiber that they represent, $$\begin{bmatrix} x \\ y \\ z \end{bmatrix}_q = \Delta d \sum_{p=0}^{q} \vec{t}_p \quad (14)$$

Substituting in the expression for the tangent vector gives, $$\begin{bmatrix} x \\ y \\ z \end{bmatrix}_q = \Delta d \sum_{p=0}^{q} \left[ \left\{ \overline{C}_0 \prod_{n=0}^{p} \overline{R}_n \right\} \cdot \begin{bmatrix} 0 \\ 0 \\ 1 \end{bmatrix} \right] \quad (15)$$

For generality, an arbitrary offset vector can be added to place the calculated coordinates into any arbitrary coordinate system.

$$\begin{bmatrix} x \\ y \\ z \end{bmatrix}_q = \Delta d \sum_{p=0}^{q} \left[ \left\{ \overline{C}_0 \prod_{n=0}^{p} \overline{R}_n \right\} \cdot \hat{z} \right] + \vec{v}_0 \quad (16)$$

where, $$\vec{v}_0 = \begin{bmatrix} x_o \\ y_0 \\ z_0 \end{bmatrix} \quad (17)$$

and, $$\hat{z} = \begin{bmatrix} 0 \\ 0 \\ 1 \end{bmatrix} \quad (18)$$

For the computation of the position and orientation of the frame of reference at the end of a segment with respect to the frame of reference at the start of the segment, $\overline{C}_0$ is the identity matrix, and $\vec{v}_0$ is a vector of zeros, which represents the frame of reference at the start of the segment. Alternatively, the computation can be carried in another base or world frame located, for instance, at the base of the kinematic chain. In this case $\overline{C}_0$ is the 3×3 matrix specifying the orientation of the frame of reference at the start of the segment with respect to the above-mentioned base frame, and $\vec{v}_0$ is the 3×1 vector specifying the position of the origin of the frame of reference at the start segment with respect to the above-mentioned base frame.

As mentioned above, in some instances the quantity $\Delta d$ is known from the property of the particular interferometer that is used. Alternatively, $\Delta d$ can be calibrated by laying the segment of fiber in a straight line, for instance with the use of a fixture, and comparing the computed segment tip position from equation 18 with the known segment physical length.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

As used herein, a Fiber Bragg Grating comprises a series of modulations of a core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the Fiber Bragg Gratings, the modulations are spaced by a known distance, thereby causing reflection of a known band of wavelengths. However, when a strain is induced on the fiber core, the spacing of the modulations will change, depending on the amount of strain in the core.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

The term "flexible" in association with a mechanical structure or component should be broadly construed. In essence, it means the structure or component can be bent without harm. For example, a flexible mechanical structure may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. As another example, a flexible mechanical structure may be continuous, such as a closed bendable tube (e.g., nitinol, polymer, and the like) or other bendable piece (e.g., kerf-cut tube, helical coil, and the like). Accordingly, a short, flexible structure may serve as, and be modeled as, a single mechanical constraint (joint) providing one or more DOFs between two links in a kinematic chain, even though the structure itself may be a kinematic chain made of several coupled links.

While the memory in FIG. 1A is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of the operations described with respect to the shape information processing module or in which computer readable code for any one or any combination of operations described with respect to the shape information processing module is stored. Some examples of computer program products are CD-ROM discs, DVD discs, flash memory, ROM cards, floppy discs, magnetic tapes, computer hard drives, servers on a network and signals transmitted over a network representing computer readable program code. A tangible computer program product comprises a tangible medium configured to store computer readable instructions for any one of, or any combination of operations described with respect to the shape information processing module or in which computer readable instructions for any one of, or any combination of operations described with respect to the shape information processing module are stored. Tangible computer program products are CD-ROM discs, DVD discs, flash memory, ROM cards, floppy discs, magnetic tapes, computer hard drives and other physical storage mediums.

In view of this disclosure, instructions used in any one of, or any combination of operations described with respect to the shape information processing module can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. An apparatus comprising:
a kinematic chain comprising a proximal link and a distal link; and
a shape-sensing segment extending through at least one of said proximal link and said distal link, the shape-sensing segment including at least one pre-set perturbation, the at least one pre-set perturbation being located and contained within one of said proximal link and said distal link, and the at least one pre-set perturbation including a bend in the shape-sensing segment.

2. The apparatus of claim 1, wherein said at least one pre-set perturbation is a permanent geometrical perturbation fixed in said shape-sensing segment.

3. The apparatus of claim 2, wherein said pre-set perturbation has a geometrical center identifiable by shape sensor measurements.

4. The apparatus of claim 2, wherein said pre-set perturbation is in a geometrical plane identifiable by shape sensor measurements.

5. The apparatus of claim 4, wherein said shape-sensing segment further includes another preset-perturbation, and wherein said another pre-set perturbation is in a second geometrical plane identifiable by said shape sensor measurements.

6. The apparatus of claim 2, further comprising:
a clamp affixed to said shape-sensing segment to form said permanent geometrical perturbation fixed in position in said shape-sensing segment.

7. The apparatus of claim 6, wherein said pre-set perturbation has a geometrical center in a fixed geometrical relationship with the one of the proximal link and the distal link.

8. The apparatus of claim 6, wherein said pre-set perturbation has a geometrical plane, identifiable by shape sensor measurements, in a fixed geometrical relationship with the one of the proximal link and the distal link.

9. The apparatus of claim 8, wherein said shape sensing segment includes another preset-perturbation, wherein said another pre-set perturbation has a second geometrical plane identifiable by said shape sensor measurements, and wherein said another pre-set perturbation is in a fixed geometrical relationship with the other of the proximal link and the distal link.

10. The apparatus of claim 1, wherein said at least one pre-set perturbation is constrained in a plane.

11. The apparatus of claim 1, further comprising:
a permanent pre-set geometrical feature fixed in position and contained within said distal link,
wherein said at least one pre-set perturbation is formed in said shape-sensing segment by said permanent pre-set geometrical feature as said permanent pre-set geometrical feature moves along said shape-sensing segment.

12. The apparatus of claim 11, wherein said permanent pre-set geometrical feature is formed in a wall of a lumen through which said shape-sensing segment passes.

13. The apparatus of claim 1, wherein at least one pre-set perturbation is positioned and contained within said proximal link.

14. The apparatus of claim 13, wherein said shape-sensing segment further comprises:
another pre-set perturbation, different from said at least one pre-set perturbation,
wherein said another pre-set perturbation is positioned and contained within said distal link; and
wherein said another pre-set perturbation includes a bend in the shape-sensing segment.

15. The apparatus of claim 13, further comprising:
another shape-sensing segment extending from a base to an entry point of said shape-sensing segment into the proximal link.

16. The apparatus of claim 1, further comprising:
an interrogator coupled to said shape-sensing segment, wherein said interrogator outputs shape information associated with the shape-sensing segment including the at least one pre-set perturbation; and
an electronic data processor, coupled to said interrogator to receive the shape information, to output relative partial-pose information of said at least one of said distal link and said proximal link.

17. The apparatus of claim 16, wherein the output relative partial-pose information is a linear displacement.

18. The apparatus of claim 16, wherein the output relative partial-pose information is an angle.

19. The apparatus of claim 16, wherein the output relative partial-pose information is three-dimensional position and orientation.

20. A method comprising:
receiving shape data, by a processor, from at least one pre-set perturbation in a shape-sensing segment, wherein said shape-sensing segment passes through at least one of a proximal link and a distal link of a kinematic chain of a surgical device, wherein said at least one pre-set perturbation is located and contained within one of said proximal link and said distal link, and wherein the at least one pre-set perturbation includes a bend in the shape-sensing segment; and
generating, by the processor from said received shape data, relative partial-pose information of at least one of said distal link and said proximal link.

21. The method of claim 20, wherein said at least one pre-set perturbation is a permanent geometrical perturbation fixed in said shape-sensing segment.

22. The method of claim 20, wherein the said distal link includes a permanent pre-set geometrical feature, and wherein said at least one pre-set perturbation is formed in said shape-sensing segment by said permanent pre-set geometrical feature as said permanent pre-set geometrical feature moves along said shape-sensing segment.

23. The method of claim 22, further comprising:
moving said distal link along said shape-sensing segment, wherein said at least one pre-set perturbation moves relative to said proximal link as distal link moves; and
said generating generates a position of said distal link relative to said proximal link.

24. The method of claim 20, wherein said at least one pre-set perturbation is located within said proximal link.

25. The method of claim 24, wherein another pre-set perturbation, different from said at least one pre-set perturbation, is included in said shape-sensing segment, wherein said another pre-set perturbation includes a bend in the shape-sensing segment, and wherein said another pre-set perturbation is located and contained within said distal link.

26. The method of claim 25, wherein said kinematic chain includes a roll joint between said proximal link and said distal link, and said output relative partial-pose information is a roll angle associated with said roll joint.

27. The method of claim 25, wherein,
said at least one pre-set perturbation is orientated in a first plane; and said another preset perturbation is orientated in a second plane wherein said output relative partial-pose information is an angle of said second plane relative to said first plane.

* * * * *